United States Patent
Schwarz et al.

(10) Patent No.: US 10,646,377 B2
(45) Date of Patent: May 12, 2020

(54) EYESHADE

(71) Applicant: Manta Sleep LLC, Jackson, WY (US)

(72) Inventors: Benjamin Schwarz, Lynnwood, WA (US); Mark Zhang, Lynnwood, WA (US)

(73) Assignee: MANTA SLEEP LLC, Jackson, WY (US)

( * ) Notice: Subject to any disclaimer, the term of this patent is extended or adjusted under 35 U.S.C. 154(b) by 134 days.

(21) Appl. No.: 15/786,574

(22) Filed: Oct. 17, 2017

(65) Prior Publication Data

US 2019/0110927 A1    Apr. 18, 2019

(51) Int. Cl.
*A61F 9/04*    (2006.01)

(52) U.S. Cl.
CPC ............... *A61F 9/045* (2013.01); *A61F 9/04* (2013.01)

(58) Field of Classification Search
CPC .. A61F 9/045; A61F 9/04; A61F 13/12; A61F 13/124; A61F 2013/00497; A61F 2013/00165; A61F 15/008
USPC ...... 2/12; D24/206; 607/109, 139, 140, 141; 128/857, 858; 602/74
See application file for complete search history.

(56) References Cited

U.S. PATENT DOCUMENTS

| | | | | |
|---|---|---|---|---|
| 1,026,272 A | * | 5/1912 | Leveque | G02C 3/003 351/156 |
| 3,140,390 A | * | 7/1964 | Smith | A61F 9/007 607/109 |
| 4,599,746 A | * | 7/1986 | Stoner | A61F 13/124 2/12 |
| 4,709,695 A | * | 12/1987 | Kohn | A61F 9/04 128/858 |
| 5,004,333 A | * | 4/1991 | Bruhl, Jr. | A61F 9/00 128/858 |
| 6,052,834 A | * | 4/2000 | Chou | A63B 33/002 2/426 |
| 6,081,934 A | * | 7/2000 | Stefanovsky | A61F 9/022 128/858 |

(Continued)

OTHER PUBLICATIONS

Adachi, T. & Sakka, S. "Dependence of the Elastic Moduli of Porous Silica Gel Prepared by the Sol-Gel Method on Heat-Treatment" J Mater Sci (1990) 25: 4732. https://doi.org/10.1007/BF01129933 (Year: 1990).*

*Primary Examiner* — Khoa D Huynh
*Assistant Examiner* — Grace Huang
(74) *Attorney, Agent, or Firm* — Chun-Ming Shih; HDLS IPR Services (57) ABSTRACT

An eyeshade (10) includes a head band (12) and two eye covers (20). The head band (12) includes a middle section (14), an end section (15) horizontally extending from the middle section (14), and at least three first hook-and-loop straps (142). Two of the three first hook-and-loop straps (142) are arranged on an inner surface (141) of the middle section (14). Each eye cover (20) includes an inner pad (22) and a covering portion (24). Each inner pad (22) includes an inner pad outer surface (221) and a depression (222). The covering portion (24) includes a cavity (241) corresponding to the depression (222) and includes a second hook-and-loop strap (242). Each of the second hook-and-loop straps (242) is removably attached to the corresponding first hook-and-loop strap (142). The eyeshade (10) has modular replaceable eye covers (20) which can be quickly attached to head band (12) to provide various functions as required.

12 Claims, 9 Drawing Sheets

(56) References Cited

U.S. PATENT DOCUMENTS

| | | | | |
|---|---|---|---|---|
| 6,098,628 | A * | 8/2000 | Funk | A61F 13/124 |
| | | | | 128/859 |
| 6,658,664 | B1 * | 12/2003 | Verhoeven | A42B 1/22 |
| | | | | 2/12 |
| 7,748,387 | B1 * | 7/2010 | Vu | A61F 9/04 |
| | | | | 128/858 |
| 8,109,964 | B2 * | 2/2012 | Payne | A61F 13/124 |
| | | | | 606/204.25 |
| 8,708,982 | B2 * | 4/2014 | Lin | A61F 9/0026 |
| | | | | 604/307 |
| 9,572,718 | B2 * | 2/2017 | Sternlight | B60N 2/882 |
| 9,724,230 | B2 * | 8/2017 | Badawi | A61F 7/02 |
| 9,999,347 | B2 * | 6/2018 | Geertsen | A61B 3/113 |
| 10,021,954 | B2 * | 7/2018 | Wardaszka | A45D 44/002 |
| 10,039,693 | B1 * | 8/2018 | Hoffman | A61H 39/04 |
| 10,285,862 | B2 * | 5/2019 | Belliappa | A61F 9/04 |
| 2003/0056281 | A1 * | 3/2003 | Hasegawa | A61F 7/02 |
| | | | | 2/428 |
| 2011/0208279 | A1 * | 8/2011 | Sanker | A61F 7/02 |
| | | | | 607/109 |
| 2016/0008175 | A1 * | 1/2016 | Bergman | A61F 9/04 |
| | | | | 2/171.2 |
| 2017/0231292 | A1 * | 8/2017 | Warren | A41D 31/102 |
| | | | | 2/69 |
| 2017/0252210 | A1 * | 9/2017 | Bruder | A61F 7/02 |

* cited by examiner

EYESHADE

TECHNICAL FIELD

The present invention relates to an eyeshade and, in particular, to an eyeshade having a modular eye covers which can be quickly attached to or detached from the eyeshade.

BACKGROUND

Sleep quality is one of the most important factors in living a healthy life. Good sleep regulates hormone production (growth hormone & melatonin), decreases stress, improves memory, and increases overall happiness. Unfortunately, due to the demands of the modern society, people are not getting enough quality sleep. This negatively impacts all aspects of life, from personal to professional.

According to research, wearing an eyeshade to create total darkness can increase melatonin production, which leads to improved sleep quality and prolonged deep sleep. However, conventional eyeshades cannot be adjusted according to individual face shape and head size, which creates discomfort and can let light leak through. Thus, an improved eyeshade that's adjustable and customizable is needed in the market.

In view of this, the inventor studied various technologies and created an effective solution in the present disclosure.

SUMMARY

It is an objective of the present invention to provide an eyeshade which has detachable modular eye covers.

It is another objective of the present invention to provide an eyeshade which has a head band that's adjustable in length to fit different head sizes.

It is an objective of the present invention to provide an eyeshade which has detachable modular eye covers that can adjust the distance between the two eyes of a wearer.

It is an objective of the present invention to provide an eyeshade which relieves the pressure on the head of a wearer and also provides a proper elastic tightening effect.

It is an objective of the present invention to provide an eyeshade which increases the friction between the eyeshade and the head of a wearer, thereby preventing the eyeshade from slipping off the head.

It is an objective of the present invention to provide an eyeshade with modular eye covers which can be quickly attached or detached from the eyeshade by means of a hook-and-loop strap, whereby the two eye covers can be adjusted to the right positions.

It is an objective of the present invention to provide an eyeshade, wherein the thickness of each eye cover of the eyeshade has variations, thus enhancing wearing comfort and avoiding pressure on the nose bridge of a wearer.

It is another objective to provide an eyeshade, wherein besides blocking out light rays, the eyeshade has various functions, such as awakening a wearer, emitting light, providing vibratory massages, providing hot/cold therapy, and playing music, by means of modular eye covers (modular units.

Accordingly, the present invention provides an eyeshade which comprises of a head band and two eye covers. The head band includes a middle section, at least one end section horizontally extending from the middle section, and at least one first hook-and-loop strap. The first hook-and-loop strap is disposed on an inner surface of the middle section. Each eye cover includes an inner pad and a covering portion enclosing the inner pad. Each inner pad includes an inner pad outer surface and a depression opposite to the inner pad outer surface of the inner pad. The covering portion includes a cavity corresponding to the depression and includes a second hook-and-loop strap disposed at one side opposite to the cavity. The second hook-and-loop strap is removably attached to the first hook-and-loop strap.

The present invention further has the following functions. The eye covers have modular replaceable designs to provide various functions according to requirement. In detail, besides blocking out light rays while sleeping, the eyeshade can provide functions such as awakening the wearer, relieving eye pressure, relaxing muscles around the eyes, improving sleep quality, improving eye health, or playing music.

BRIEF DESCRIPTION OF THE DRAWINGS

The disclosure will be more fully understood in the detailed description, and the drawings given herein below is for illustration only, and thus does not limit the disclosure, wherein.

DETAILED DESCRIPTION

Detailed descriptions and technical contents of the present invention are illustrated below in conjunction with the accompany drawings. However, it is to be understood that the descriptions and the accompanying drawings disclosed herein are merely illustrative and exemplary and not intended to limit the scope of the present invention.

Figure 1:
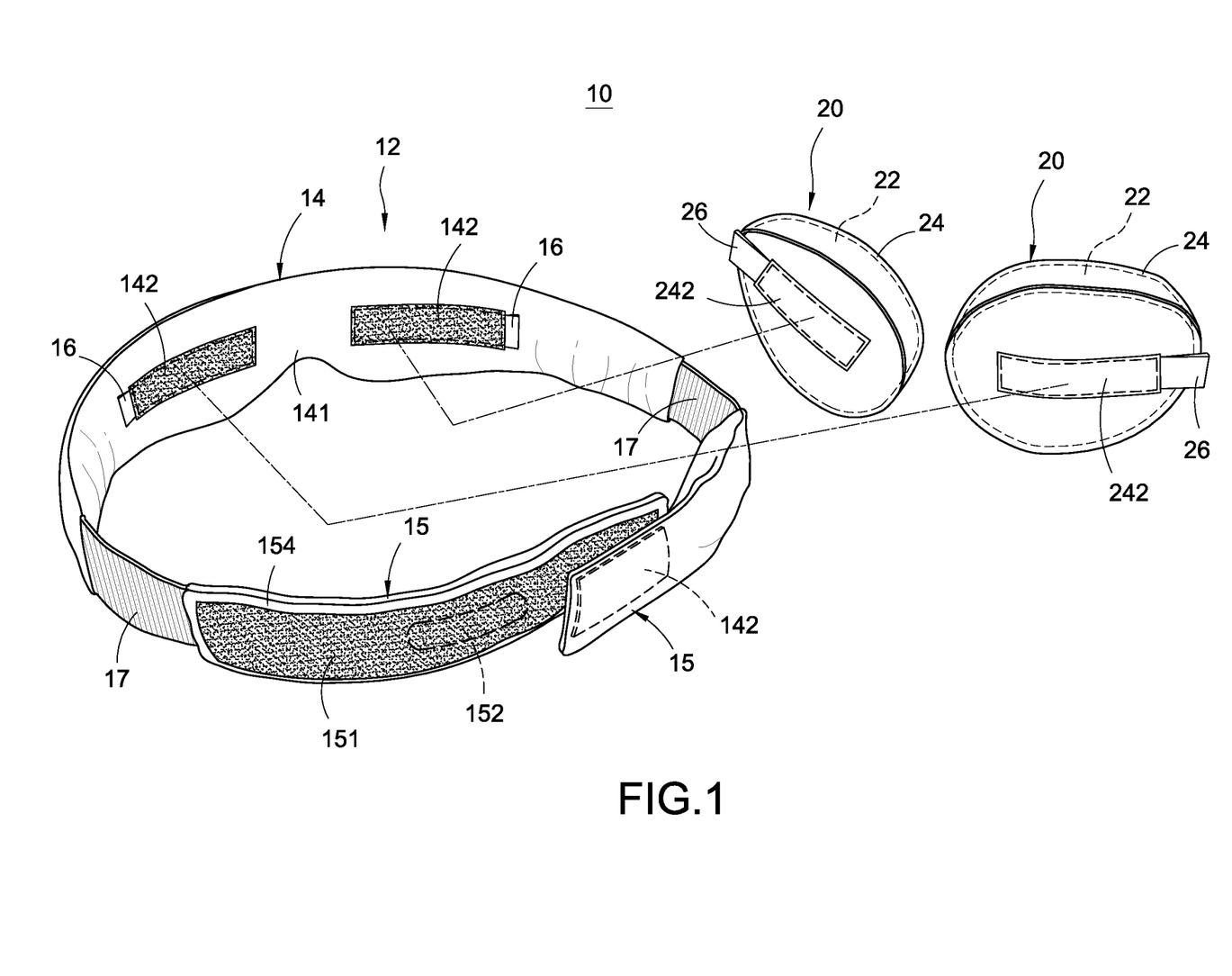
FIG. 1 is an exploded view illustrating an eyeshade of the present invention.

Please refer to FIG. 1 which is an exploded view illustrating an eyeshade of the present invention. The present invention provides an eyeshade 10 including a head band 12 and two detachable eye covers 20. The head band 12 shown in FIG. 1 is, including but not limited to, fabric or cloth for wearing comfort. Furthermore, the eyeshade 10 has various interchangeable design eye covers 20. In the embodiment of FIG. 1, the eyeshade 10 is primarily a sleep eyeshade. However, in alternative embodiments, the eyeshade 10 utilizes different eye covers 20 to provide various functions such as emitting light or playing music to awake a user, cool/hot therapy, and vibratory massage. The structure of the eyeshade 10 is further detailed hereinafter.

As shown in FIG. 1, the head band 12 includes a middle section 14, two end sections 15 horizontally extending from the middle section 14, and at least three first hook-and-loop straps 142. Two of the at least three first hook-and-loop straps 142 are disposed on an inner surface 141 of the middle section 14. The two end sections 15 are positioned around a head of a wearer.

In this embodiment, it is preferable that, the eyeshade 10 includes two end sections 15 horizontally extending from the middle section 14 to two ends of the head band 12, and the eyeshade 10 includes multiple first hook-and-loop straps 142. In detail, one of the at least three first hook-and-loop straps 142 is disposed on any end section 15 to be attached to the other end section 15. Furthermore, it is preferable that the number of the first hook-and-loop straps 142 disposed on the inner surface 141 of the middle section 14 is two, and these two hook-and-loop straps 142 are spaced apart and arranged corresponding to the two eye covers 20 respectively, so that the wearer's nose bridge can be correspondingly in contact with the inner surface 141 for wearing comfort.

Figure 11A:
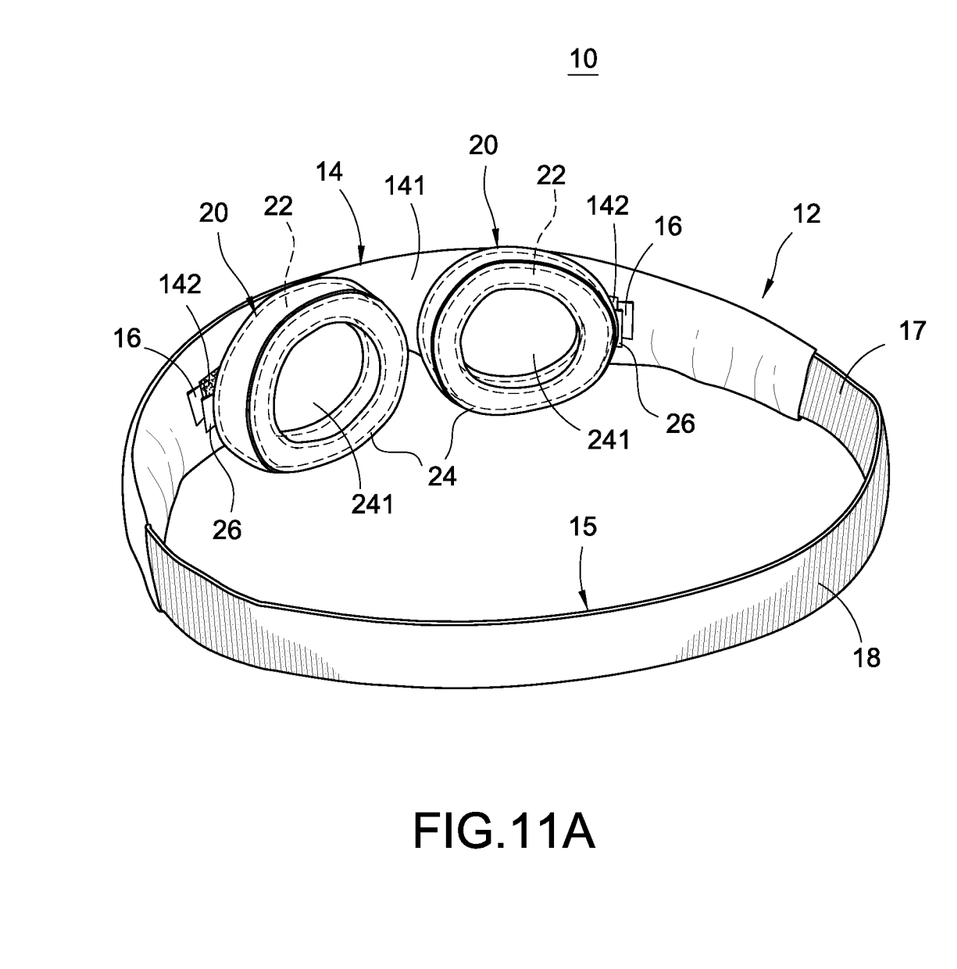
FIG. 11A is a schematic view illustrating a head band of the eyeshade according to another embodiment of the present invention.
Figure 11B:
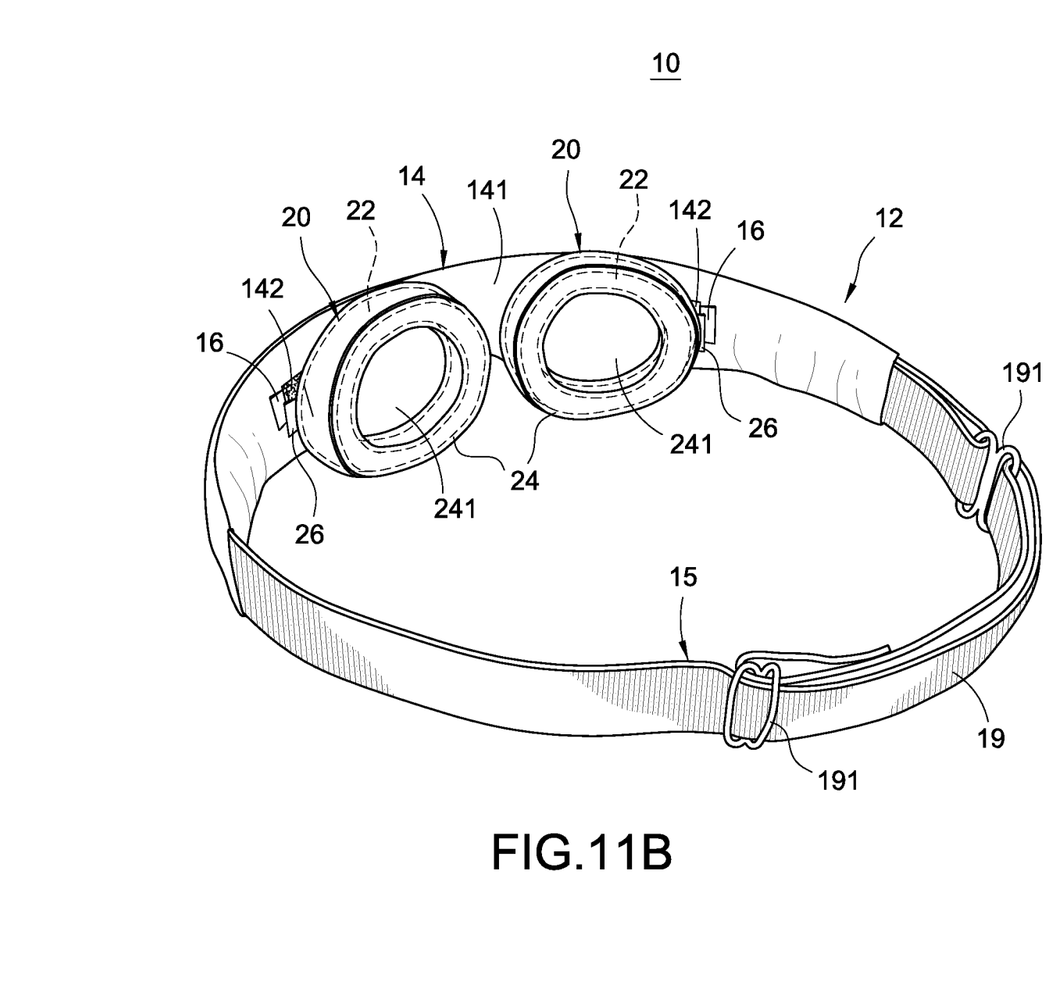
FIG. 11B is a schematic view illustrating the head band of the eyeshade according to still another embodiment of the present invention.

However, in the embodiment shown in FIG. 11A, the eyeshade 10 includes a single end section 15 which is a stretchable section 18 elastically stretchable around the head of the wearer. The stretchable section 18 is made of nylon, elastic yarns, or other suitable material, and the stretchable section 18 is positioned around the head and is stretchable to fit heads of different sizes. In the embodiment of FIG. 11B, the end section 15 is a surrounding section 19 having at least one loop fastener 191. The surrounding section 19 is inserted through the loop fastener 191 and is adjustable to fit heads of different sizes. In FIG. 11B, the eyeshade 10 preferably has two surrounding sections 19 made of non-elastic fabric; however, the present invention is not limited in this regard.

Figure 2:
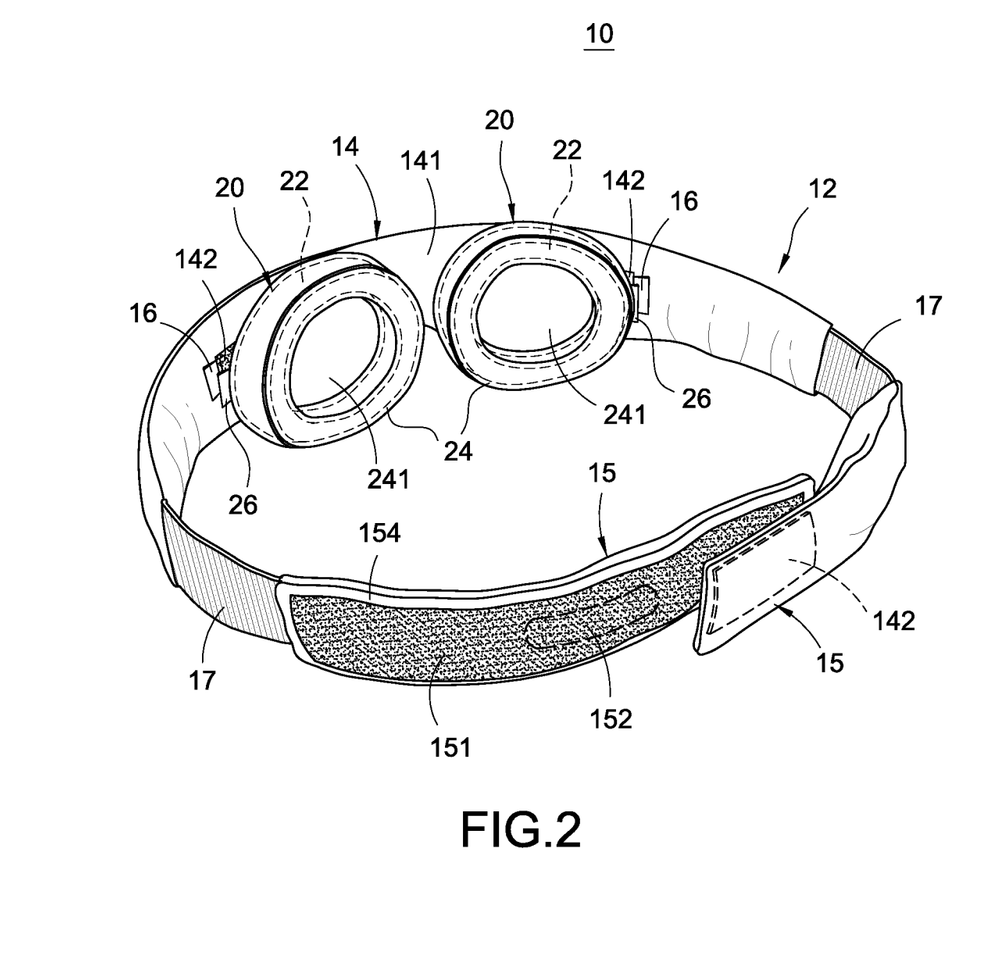
FIG. 2 is a perspective view illustrating the eyeshade.
Figure 3:
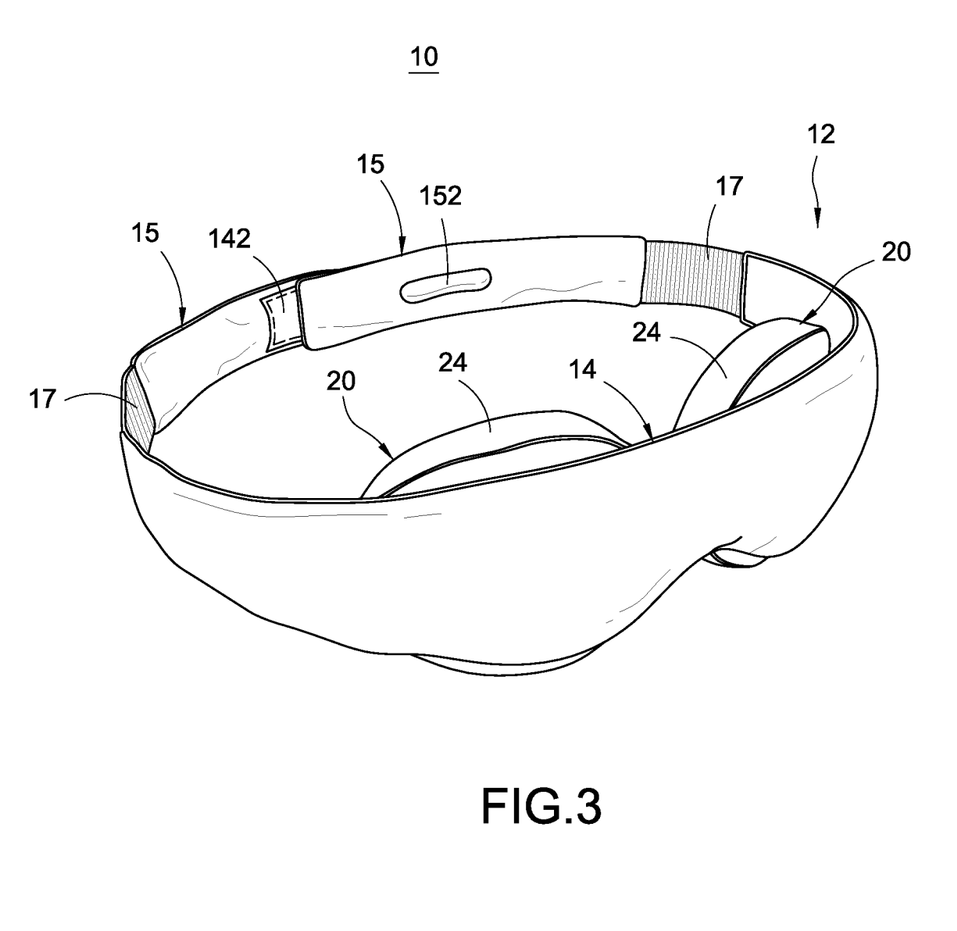
FIG. 3 is another perspective view illustrating the eyeshade.

Referring to FIGS. 2 and 3, a surface 154 of the end section 15 having no first hook-and-loop straps 142 includes a second hook-and-loop strap 151 and an anti-slip strip 152 on one side opposite to the second hook-and-loop strap 151. The anti-slip strip 152 is, for example, a plastic plate, a rubber plate or other suitable material for increasing friction between the eyeshade 10 and the head, i.e. reducing slippage of the head band 12 on the head. However, in alternative embodiments, one or more additional anti-slip strips 152 can be disposed on the head band 12 or other positions to increase friction.

The second hook-and-loop strap 151 is used to be attached to the end section 15 having the first hook-and-loop strap 142. In the embodiment shown in FIGS. 1 to 3, the second hook-and-loop strap 151 is preferably longer than the first hook-and-loop strap 142, so that the wearer can easily adjust the length of the head band 12 according to his/her head size, face contours, or the distance between the two eyes. However, in alternative embodiments, the second hook-and-loop strap 151 can be replaced by other material such as a fleece fabric which also can be attached to the first hook-and-loop strap 142.

Furthermore, an elastic section 17 is connected between the middle section 14 and each end section 15. The elastic section 17 is connected to the middle section 14 and each end section 15 by, for example, stitching. The elastic section 17 is made of nylon, elastic yarns, or other suitable material to relieve pressure to the head and also provides proper elastic tightening effect. Each first hook-and-loop strap 142 and each second hook-and-loop strap 151 are a pair of hook and loop fastening elements attachable to each other. The hook-and-loop straps employ conventional techniques, so a detailed description thereof is omitted for brevity.

Figure 4:
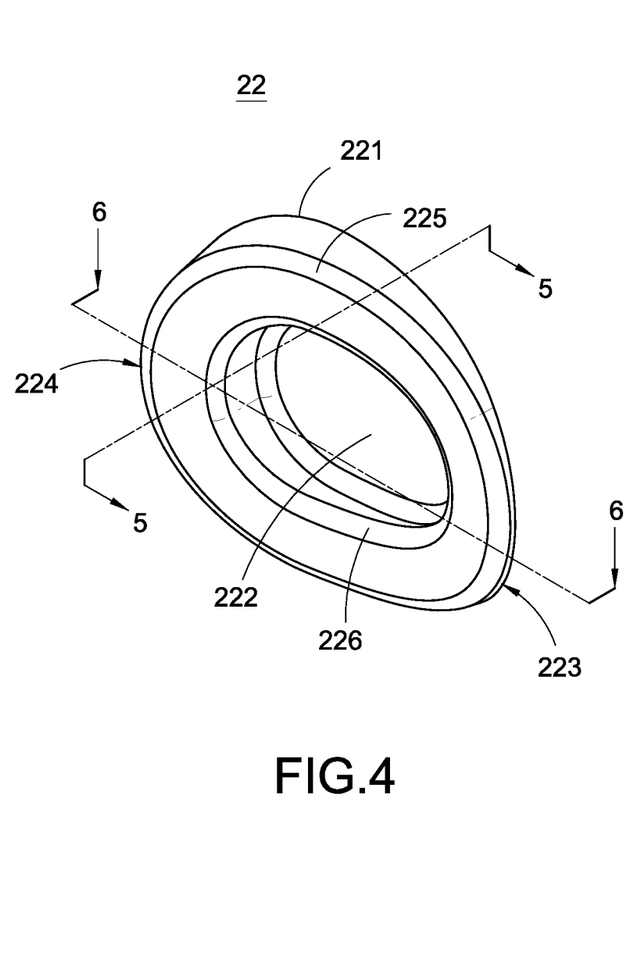
FIG. 4 is a perspective view illustrating an inner pad of the eyeshade.
Figure 5:
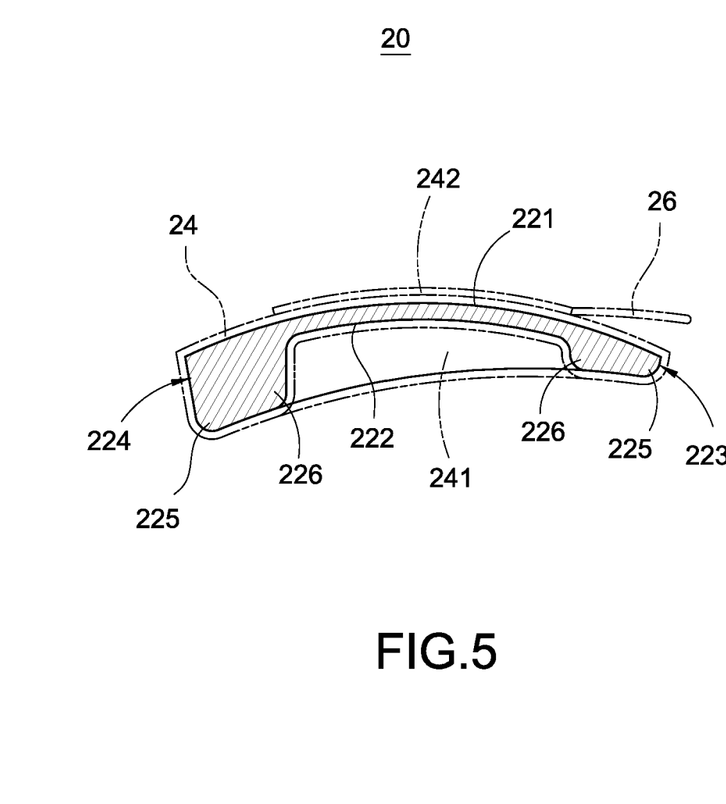
FIG. 5 is a cross-sectional view illustrating an eye cover of the eyeshade.

Referring to FIGS. 4 and 5, each eye cover 20 includes an inner pad 22 and a covering portion 24 enclosing the inner pad 22. Each inner pad 22 includes an inner pad outer surface 221 and a depression 222 corresponding to the inner pad outer surface 221. The covering portion 24 has a first forming a cavity 241 corresponding to the depression 222 and a second side opposite to the first side being disposed with a second hook-and-loop strap 242, wherein the second hook-and-loop strap 242 is removably attached to the first hook-and-loop strap 142. Accordingly, each eye cover 20 can be rapidly attached to or detached from the head band 12, and the two eye covers 20 can be adjusted in position quickly.

In the embodiment of FIG. 4, each inner pad 22 has a first end 223 and a second end 224 opposite to each other. A thickness of each inner pad 22 gradually increases from the first end 223 to the second end 224. A depth of the depression 222 gradually increases from the first end 223 to the second end 224. To fit eye and facial configurations of all wearers and to increase wearing comfort and avoid pressure on each wearer's nose, the respective second ends 224 with thicker thickness are arranged corresponding to each other in spaced-apart relationship and are attached to the first hook-and-loop straps 142 on the middle section 14 by means of the second hook-and-loop straps 242.

Figure 6:
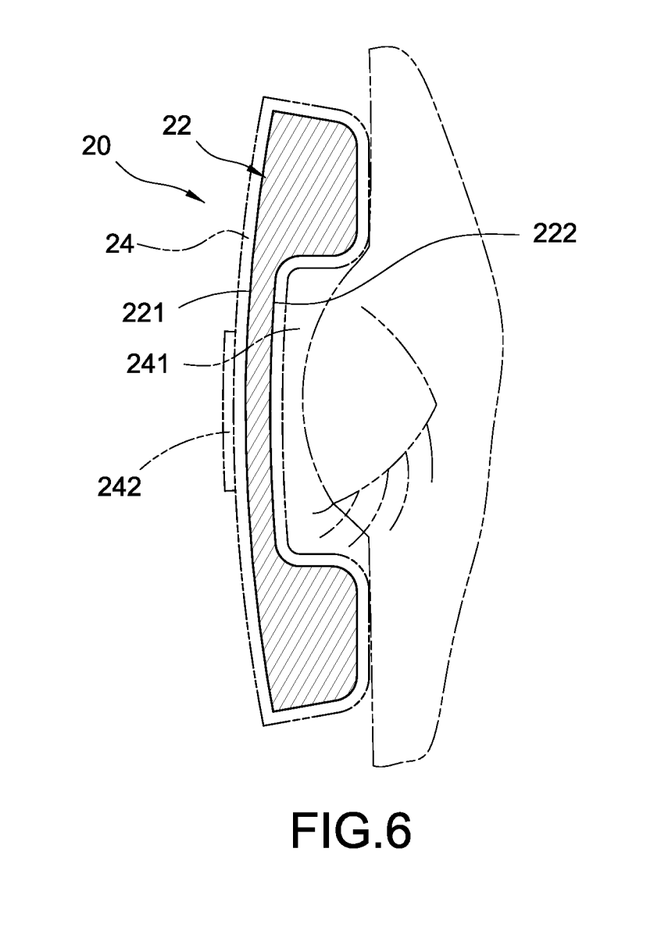
FIG. 6 is another cross-sectional view illustrating the eye cover of the eyeshade.

Furthermore, the inner pad outer surface 221 of each inner pad 22 preferably has an arc shape. An outer rim 225 of the first end 223 and the second end 224 and an inner rim 226 of the depression 222 each have an arc shape, as shown in FIG. 6. In other words, the inner rim 226 and the outer rim 225, arranged close to a face of the wearer, each preferably have an arc shape, so that the eye cover 20 exerts less pressure and causes no discomfort to the wearer's face even if the eye cover 20 contacts or is attached on the wearer's face for a long time. Moreover, the inner pad 22 preferably has an arc outline, and the inner pad outer surface 221 has an arc shape, so the depression 222 and the cavity 241 have a larger inner space to accommodate the wearer's eyelashes and eyelid and also prevent the eyelashes and eyelids from contacting the boundary of the cavity 241.

In detail, the inner pad 22 preferably is ergonomically designed and consists of an elastic material such as a breathable foam material. For example, the inner pad 22 is covered by the covering portion 24 made of dark or black fabric, cloth, or other suitable material for protection against light rays. Furthermore, after the inner pad 22 is covered by the covering portion 24, the wearer may have difficulty determining which end of the inner pad 22 is thicker by visually observing it. Therefore, the head band 12 further includes two first sign elements 16 in order to allow the wearer to visually determine the orientation of the inner pad 22 and then attach the thicker second end 224 of the inner pad to a place on the first hook-and-loop strap 142 closer to his/her nose bridge when to wear the eyeshade 10. Each eye cover 20 has a second sign element 26 corresponding to a respective corresponding one of the first sign elements 16, thereby reminding the wearer to attach the eye covers 20 with correct orientation onto the respective first hook-and-loop straps 142.

As shown in FIGS. 1, 2 and 6, the first sign elements 16 are preferably stitched to the inner surface 141 of the middle section 14 and are arranged in a horizontal direction of the respective first hook-and-loop straps 142. The second sign elements 26 are disposed adjacent to the respective first ends 223, and the second sign elements 26 and the second hook-and-loop straps 242 are stitched to the respective covering portions 24. Furthermore, for reminder purposes, the first sign elements 16 are exposed and arranged toward the respective end sections 15, and the second sign elements 26 are exposed and arranged toward the respective corresponding first ends 223.

In the present embodiment, the first sign elements 16 and the second sign elements 26 preferably are, including but not limited to, same-color cloth, same-color labels, or other suitable same-color elements. However, the first sign elements 16 and the second sign elements 26 are preferably of different color from the head band 12 and the eye covers 20, thereby enhancing the visibility, so that the wearer can easily and correctly attach the eye covers 20 to the head band 12.

Figure 7:
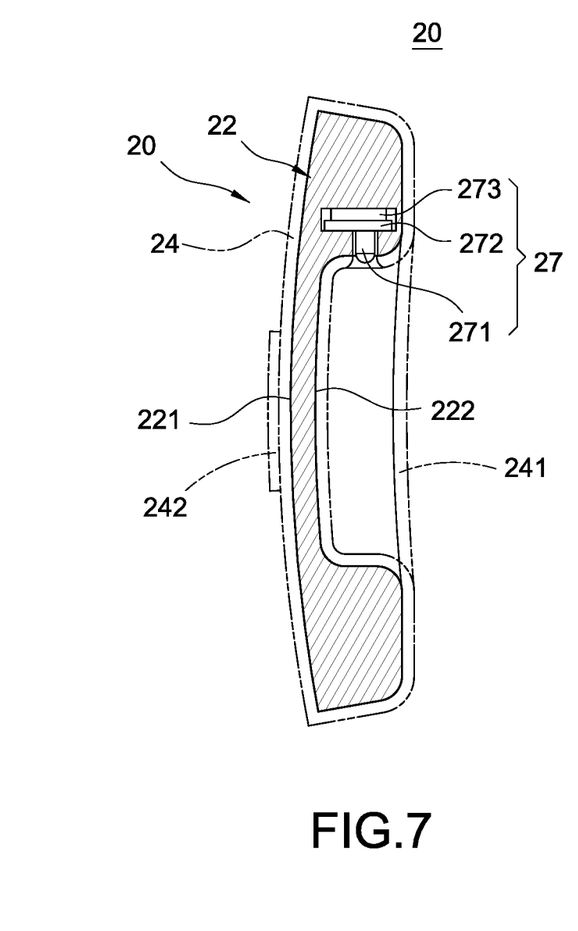
FIG. 7 is a cross-sectional view illustrating the eye cover having a light source module.

Referring to FIG. 7, the inner pad 22 of each eye cover 20 includes a light source module 27. The light source module 27 includes a light emitting diode (LED) 271 disposed corresponding to the depression 222, a circuit board 272 coupled to the LED 271, and a power supply unit 273 coupled to the circuit board 272, so that each eye cover 20 can also emit light to awaken the wearer. The power supply unit 273 is, for example, a battery or other suitable power supply element.

Figure 8:
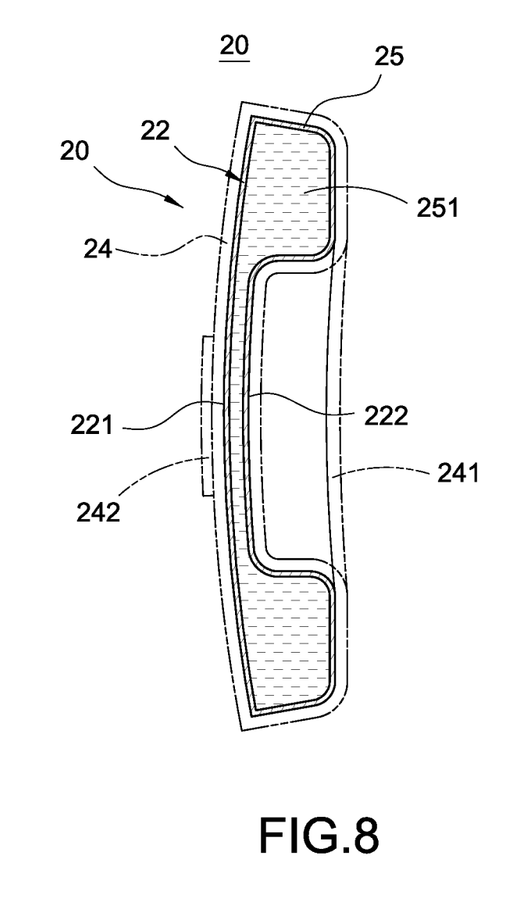
FIG. 8 is a cross-sectional view illustrating the eye cover having a hot/cold pack.

As shown in FIG. 8, the inner pad 22 of each eye cover 20 can also be a hot/cold pack 25. A liquid/gel material 251 is disposed inside the hot/cold pack 25. The inner pads 22 can be used for hot/cold therapy by adding hot/cold water into the hot/cold pack 25 or by microwaving it or by placing it in a refrigerator to freeze it.

Figure 9:
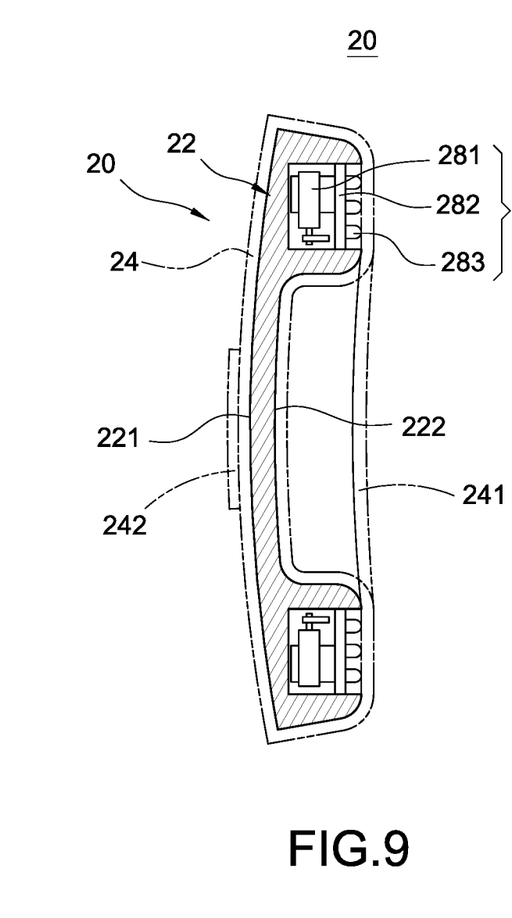
FIG. 9 is a cross-sectional view illustrating the eye cover having a vibratory massage function.

Referring to FIG. 9, the inner pad 22 of each eye cover 20 includes at least one vibratory massage module 28. In the present embodiment, there are preferably two vibratory massage modules 28 disposed at two ends of the inner pad 22, respectively. The vibratory massage module 28 includes an actuator 281, at least one massage element 283 connected to the actuator 281 and a power supply unit 282 coupled to the actuator 281 for providing vibratory massage. The power supply unit 282 is, for example, a battery or other suitable power supply element.

Figure 10:
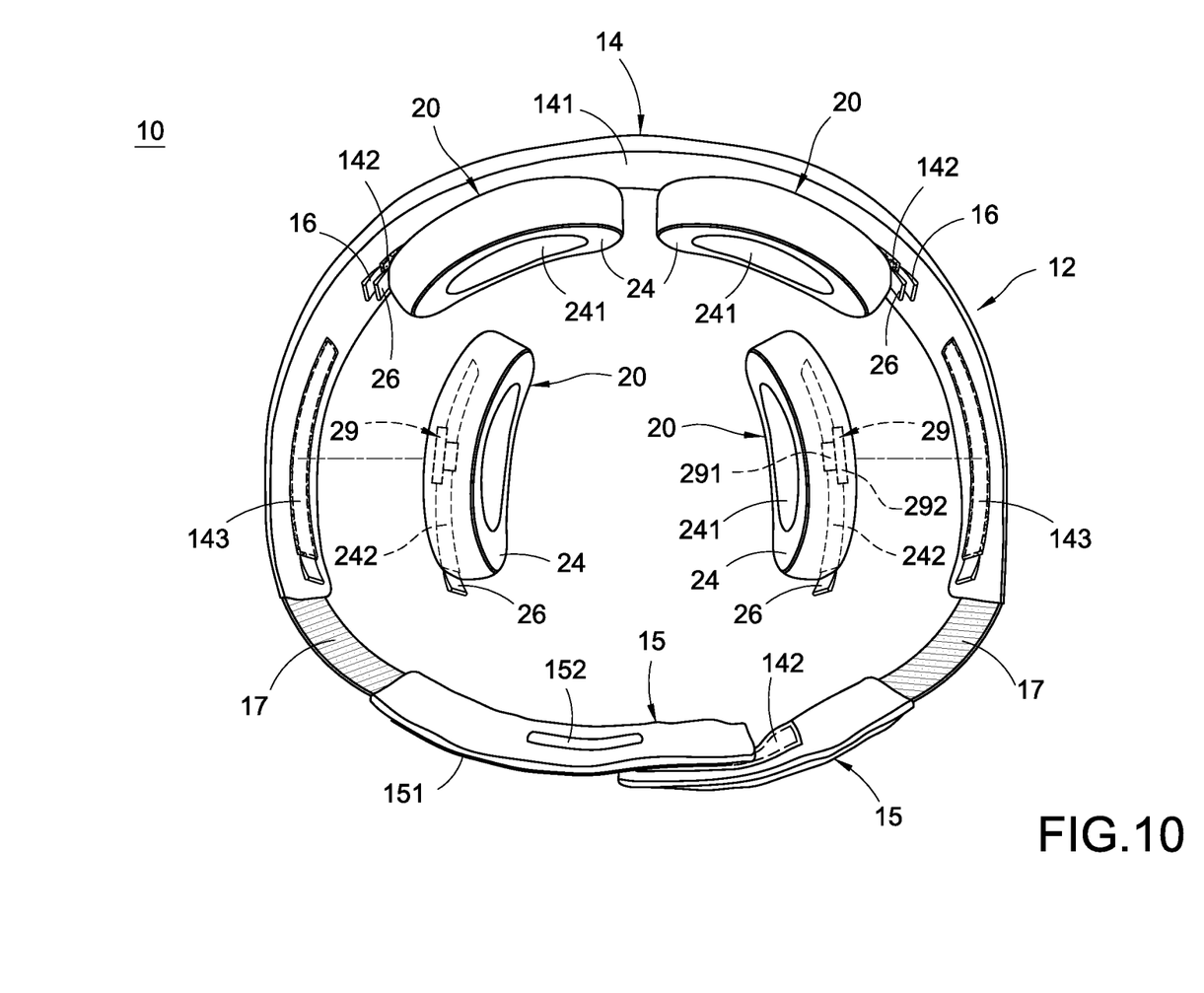
FIG. 10 is a cross-sectional view illustrating the eye cover having an earpiece module.

Referring to FIG. 10, in the present embodiment, the eyeshade 10 further includes two earpiece modules 29. The two earpiece modules 29 are disposed between each eye cover 20 and each end section 15, corresponding to two ears of the wearer. Each earpiece module 29 includes a speaker 291 and a power supply unit (e.g. a battery) 292 to play music or notification sound. In the present embodiment, each earpiece module 29 has a similar structure as the eye cover 20. To be specific, each earpiece module 29 similarly has the inner pad 22 and the covering portion 24 enclosing the inner pad 22. The speaker 291 and the power supply unit 292 are disposed inside the inner pad 22, and the remaining structure details have been described in the foregoing embodiments.

The head band 12 further includes a third hook-and-loop strap 143 corresponding to the second hook-and-loop strap 242 of each earpiece module 29 to facilitate rapid attachment or detachment of each earpiece module 29 from the head band 12 and to enable the user to quickly adjust each earpiece module 29 in right place. In FIG. 10, the third hook-and-loop strap 143 and the second hook-and-loop strap 242 can be hook-and-loop straps attachable to each other.

In the embodiment shown in FIGS. 7 to 10, the eyeshade 10 has interchangeable modular eye covers 20 with various functions such as emitting light, awakening the wearer, hot/cold therapy, vibratory massages, and playing music. Each eye cover 20 can be replaced with a different eye cover 20 to provide different functions according to demands and environment to satisfy individual requirement. To be specific, the present invention not only serve as a sleep eyeshade but also serve to awaken the wearer, relieve eye pressure, relax muscles around eyes, improve sleep quality, improve eye health, play music, etc.

Moreover, each first hook-and-loop strap 142, each second hook-and-loop strap 242, and each third hook-and-loop strap 143 are fastened to the head band 12 by, preferably, stitching. However, in alternative embodiment, each first hook-and-loop strap 142, each second hook-and-loop strap 242, and each third hook-and-loop strap 143 can be fastened to the head band 12 by means of a double-sided adhesive tape or other suitable method; the present invention is not limited in this regard.

It is to be understood that the above descriptions are merely the preferable embodiments of the present invention and are not intended to limit the scope of the present invention. Equivalent changes and modifications made in the spirit of the present invention are regarded as falling within the scope of the present invention.

What is claimed is:

1. An eyeshade consisting of:
    a head band (12) including a middle section (14), two end sections (15) horizontally extending from the middle section (14), and at least three first hook-and-loop straps (142), wherein two of the at least three first hook-and-loop straps (142) are disposed on an inner surface (141) of the middle section (14); and
    two independent eye covers (20) separated from each other, each of the eye covers (20) including an inner pad (22) and a covering portion (24) enclosing the inner pad (22), each of the inner pads (22) including an inner pad outer surface (221) and a depression (222) opposite to the inner pad outer surface (221), each of the covering portions (24) having a first side forming a cavity (241) corresponding to the corresponding depression (222), and a second side opposite to the first side being disposed with a second hook-and-loop strap (242), wherein each of the two second hook-and-loop straps (242) is removably attached to the corresponding two of the at least three first hook-and-loop straps (142),
    wherein each of the inner pads (22) includes a first end (223) and a second end (224) opposite to each other, a thickness of each inner pad (22) gradually increases from the first end (223) to the second end (224), and a depth of the depression (222) gradually increases from the first end (223) to the second end (224);
    wherein the respective second ends (224) of the inner pads (22) of the two eye covers (20) are arranged corresponding to each other and are attached to the two of the at least three first hook-and-loop straps (142) on the middle section (14) by means of the respective second hook-and-loop straps (242);
    wherein each of the inner pad outer surfaces (221) has an arc shape, and an edge of each of the first ends (223) of the inner pads (22) and an edge of each of the second ends (224) of the inner pads (22) both are formed in arc shape;
    wherein the circular band (12) includes two first sign elements (16), and each eye cover (20) includes a second sign element (26) corresponding to one of the two first sign elements (16), so that each eye cover (20) is attached with correct orientation onto the middle section (14); the first sign elements (16) arranged along a horizontal direction of the respective two of the at least three first hook-and-loop straps (142) are stitched onto the inner surface (141), the two second sign elements (26) are disposed adjacent to the two first ends (223) respectively, and the second sign elements (26) and the respective second hook-and-loop straps (242) are stitched to the respective covering portions (24); and the first sign elements (16) are exposed and arranged toward the respective end sections (15), and the two second sign elements (26) are exposed and arranged toward the corresponding first ends (223) respectively, wherein the first sign elements (16) and the second sign elements (26) are same-color cloth, same-color stickers, or same-color labels.

2. The eyeshade according to claim 1, wherein one of the at least three first hook-and-loop straps (142) is disposed on one of the two end sections (15) to be attached to the other end section (15).

3. The eyeshade according to claim 2, wherein a second hook-and-loop strap (151) is disposed on a surface of the end section (15) having none of the at least three first hook-and-loop straps (142), an anti-slip strip (152) is disposed on one side of this end section (15) opposite to the second hook-and-loop strap (151), the second hook-and-loop strap (151) is attached to the other end section (15) having the one of the at least three the first hook-and-loop straps (142), and the anti-slip strip (152) is a plastic plate or a rubber plate.

4. The eyeshade according to claim 2, wherein an elastic section (17) is connected between the middle section (14) and each end section (15).

5. The eyeshade according to claim 2, further comprising two earpiece modules (29) disposed between each eye cover (20) and each end section (15), each earpiece module (29) including a speaker (291) and a power supply unit (292) in an inner pad (22) and including a covering portion (24) which encloses the inner pad (22), wherein the head band (12) further includes two third hook-and-loop straps (143) corresponding to the two second hook-and-loop straps (242) respectively, and the third hook-and-loop strap (143) and the second hook-and-loop strap (242) are a pair of hook and loop fastening elements attachable to each other.

6. The eyeshade according to claim 2, wherein the first hook-and-loop strap (142) and the second hook-and-loop strap (242) are a pair of hook and loop fastening elements attachable to each other.

7. The eyeshade according to claim 1, wherein the covering portion (24) consists of fabric or cloth.

8. The eyeshade according to claim 1, wherein the eyeshade (10) includes the two of the at least three first hook-and-loop straps (142) on the middle section (14), and the two of the at least three first hook-and-loop straps (142) are arranged spaced apart and disposed corresponding to the two eye covers (20) respectively.

9. The eyeshade according to claim 1, wherein the first hook-and-loop strap (142) and the second hook-and-loop strap (242) are a pair of hook and loop fastening elements attachable to each other.

10. The eyeshade according to claim 1, wherein the inner pad (22) of each eye cover (20) includes a light source module (27), the light source module (27) includes a light emitting diode (271) disposed corresponding to the depression (222), a circuit board (272) coupled to the light emitting diode (271), and a power supply unit (273) coupled to the circuit board (272).

11. The eyeshade according to claim 1, wherein the inner pad (22) of each eye cover (20) is a hot/cold pack (25), and a liquid/gel material (251) is disposed inside the hot/cold pack (25).

12. The eyeshade according to claim 1, wherein the inner pad (22) of each eye cover (20) includes at least one vibratory massage module (28), the vibratory massage module (28) includes an actuator (281), at least one massage element (283) connected to the actuator (281), and a power supply unit (282) coupled to the actuator (281).

\* \* \* \* \*